United States Patent [19]

Anderhub et al.

[11] Patent Number: 5,395,364
[45] Date of Patent: Mar. 7, 1995

[54] ENDOSCOPIC INSTRUMENT INCORPORATING AN ELASTOMERIC FLUID SEAL

[75] Inventors: Otto E. Anderhub; Michael S. McBrayer, both of Miami, Fla.

[73] Assignee: Symbiosis Corporation, Miami, Fla.

[21] Appl. No.: 74,790

[22] Filed: Jun. 10, 1993

[51] Int. Cl.6 .................. A61B 17/28; A61B 17/32
[52] U.S. Cl. ..................... 606/51; 606/52; 606/174; 606/205; 128/751
[58] Field of Search ............... 606/205, 206, 207, 208, 606/170, 171, 174, 51, 52, 46, 47; 128/751

[56] References Cited

U.S. PATENT DOCUMENTS

| | | | |
|---|---|---|---|
| 3,964,468 | 6/1976 | Schulz | 128/2 B |
| 4,649,938 | 3/1987 | McArthur | 128/785 |
| 4,857,062 | 8/1989 | Russell | 604/256 |
| 4,898,157 | 2/1990 | Messorghli et al. | 606/147 |
| 4,953,559 | 9/1990 | Salerno | 128/751 |
| 5,035,248 | 7/1991 | Zinnecker | 128/751 |
| 5,041,111 | 8/1991 | Bauer et al. | 606/47 |
| 5,171,256 | 12/1992 | Smith et al. | 606/205 |
| 5,197,963 | 3/1993 | Parins | 606/46 |
| 5,205,831 | 4/1993 | Ryan et al. | 604/167 |

Primary Examiner—Michael H. Thaler
Attorney, Agent, or Firm—David P. Gordon

[57] ABSTRACT

Elastomeric fluid seals for endoscopic instruments include a single piece of molded elastomer surrounding a pushrod and placed with the outer tube or clevis of the instrument, thereby sealing the annular space between the pushrod and the outer tube. The dimensions of the seals are chosen such that they fit snugly inside the tube or clevis of the endoscopic instrument and the push rod of the endoscopic instrument fits snugly through the seal. When placed within the tube, the seal is preferably formed as a cylinder with a radially inward extending toroidal ring. As the push rod is moved through the fluid seal, the toroidal ring is pressed in an axial direction and thereby exerts a radially outward force on the seal which keeps the seal from moving inside the tube. When placed within the clevis, the seal is preferably formed as an adjacent cylinder and semi-cylinder which is inserted in a radial bore overlapping the proximal portion of the U-shaped cut-out of the clevis. The fluid seal used in the clevis preferably has a stepped inner bore through which the push rod passes. Regardless of whether it is used in the tube or clevis, the seal is preferably formed from a molded elastic polymer.

8 Claims, 4 Drawing Sheets

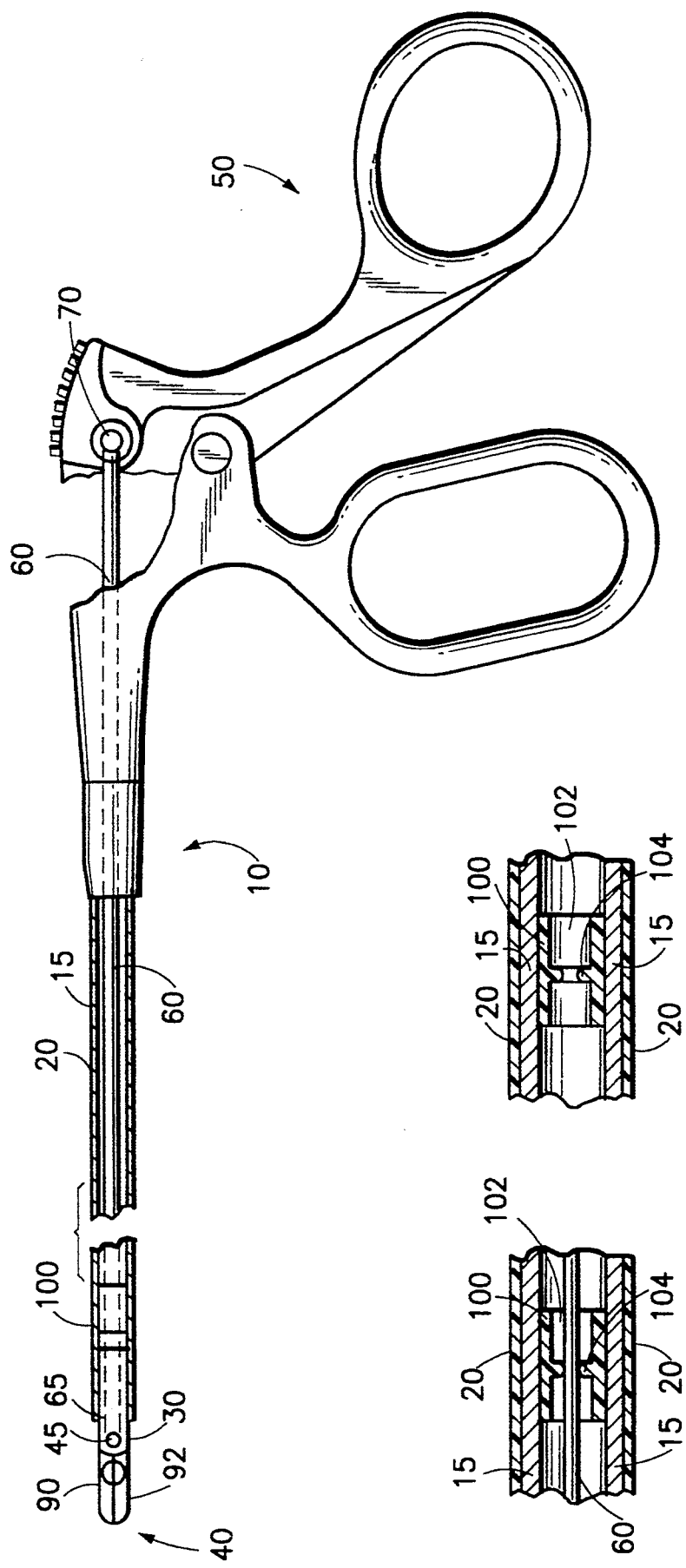

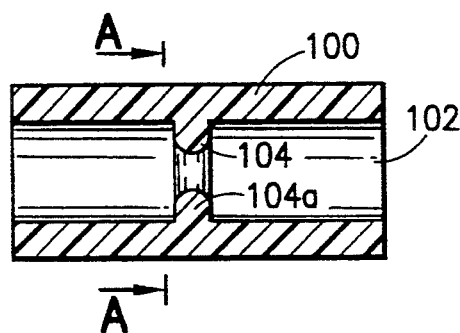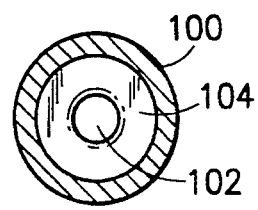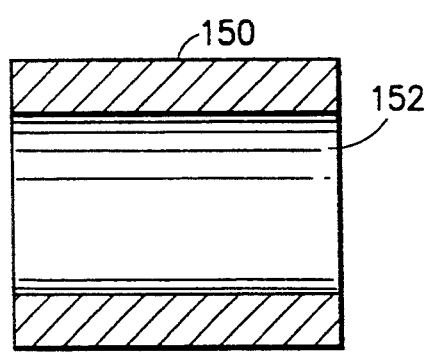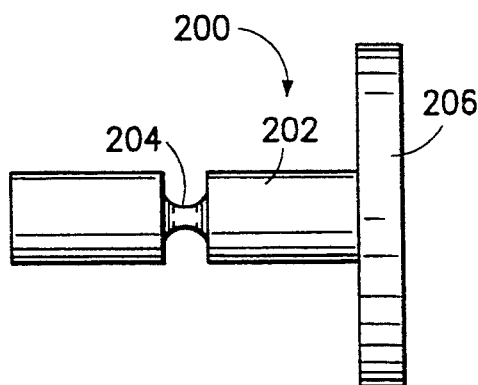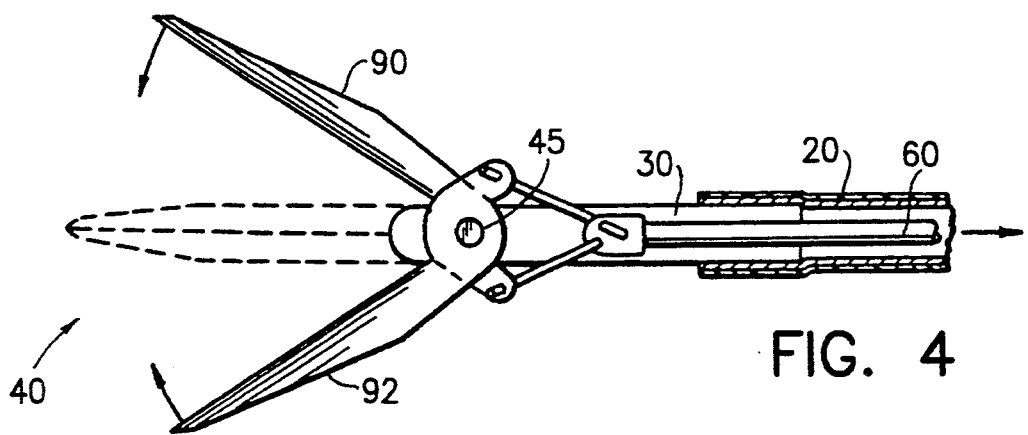

ENDOSCOPIC INSTRUMENT INCORPORATING AN ELASTOMERIC FLUID SEAL

This invention relates to Ser. No. 07/922,023 now U.S. Pat. No. 5,331,971 which is a continuation of, among others, Ser. No. 07/680,392 issued as U.S. Pat. No. 5,192,298. The complete text of Ser. No. 07/922,023 is hereby incorporated by reference in its entirety herein.

BACKGROUND OF THE INVENTION

1. Field of the Invention

The invention relates to endoscopic surgical tools. More particularly, the invention relates to an elastomeric seal between the push rod and outer tube of endoscopic instruments such as laparascopic instruments.

2. State of the Art

Endoscopic surgery is widely practiced throughout the world today and its acceptance is growing rapidly. In general, endoscopic surgery involves one or more incisions made by trocars where trocar tubes are left in place so that endoscopic surgical instruments may be inserted through the tubes. A camera, lens, or other viewing device is often inserted through one trocar tube, while a cutter, dissector, or other surgical instrument is inserted through another trocar tube for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon via the viewing device in place in one of the trocar tubes.

Trocar tubes are usually provided with a proximal elastomeric seal to prevent gas and other fluids from escaping from the body cavity while allowing endoscopic instruments to be inserted through the trocar tubes. These seals are only partially effective, however, because of the nature of the endoscopic instruments used. In particular, most endoscopic instruments include a hollow outer tube, a push rod which extends through the tube, and an actuating means engaging the tube and the push rod. The actuating means imparts reciprocal axial motion to the push rod, and hence to the end effectors (cutters, grippers, dissectors, etc.) which are coupled to the push rod and the tube, such that the end effectors are moved. When inserted through a trocar tube, the endoscopic instrument tube is surrounded by the elastomeric seal of the trocar tube. This prevents gas and other fluids from escaping through the annular space between the instrument tube and the trocar tube. The inventor has realized, however, that the annular space between the push rod and the instrument tube still presents a clear, albeit small, path for fluids, and that is why the proximal trocar tube seal is only partially effective. Gas and other fluids can enter the endoscopic instrument tube and pass through to the actuating means. The escape of gas can desufflate the surgical site requiring additional insufflation of gas.

SUMMARY OF THE INVENTION

It is therefore an object of the invention to provide a fluid seal to seal the annular space between the tube and push rod of an endoscopic instrument.

It is also an object of the invention to provide an endoscopic instrument incorporating a fluid seal between the tube and push rod.

It is another object of the invention to provide a simple and inexpensive method for manufacturing a fluid seal for use in an endoscopic instrument.

It is still another object of the invention to provide a fluid seal for use in an endoscopic instrument which effectively seals the annular space between push rod and tube but which does not impede operation of the instrument.

It is a further object of the invention to provide a fluid seal for use in an endoscopic instrument which is easy to install into an endoscopic instrument and which stays in place therein.

In accord with these objects which will be discussed in detail below, an endoscopic instrument is provided with an outer tube, a push rod extending through the outer tube, actuation means coupled to the push rod, end effectors coupled to the push rod and outer tube, and a fluid seal which fits snugly inside the outer tube and having a hole through which the push rod extends. The fluid seal preferably comprises a single piece of molded elastomer formed as a cylinder with a radially inward extending ring. The push rod of the endoscopic instrument fits snugly through the radially inward extending ring.

Preferred aspects of the invention include: forming the seal as a silicon seal having a 1:10 ratio mixture of curing agent and Dow Corning SILASTIC which when cured has enough elasticity to elongate approximately 100% without tearing; shaping the radially inward extending ring as a toroid; and locating the inwardly extending ring in the axial middle of the seal. With such a seal and arrangement, as the push rod is moved through the fluid seal, the toroidal ring is pressed in an axial direction and thereby exerts a radially outward force on the seal which keeps the seal from moving inside the tube.

Additional objects and advantages of the invention will become apparent to those skilled in the art upon reference to the detailed description taken in conjunction with the provided figures.

BRIEF DESCRIPTION OF THE DRAWINGS

FIG. 1 is a side elevation view in partial cross section of an endoscopic instrument incorporating a first embodiment of the fluid seal of the invention;

FIG. 1a and 1b are magnified longitudinal cross sectional views of the fluid seal of FIG. 1 inside the tube of the endoscopic instrument;

FIG. 2 is a further magnified longitudinal cross sectional view of the fluid seal of FIG. 1;

FIG. 2a is a sectional view along line A—A in FIG. 2;

FIG. 3 is a longitudinal cross section of a mold for making the fluid seal of FIG. 1;

FIG. 3a is a side elevation view of a mold insert used with the mold of FIG. 3 for molding the fluid seal of FIG. 1;

FIG. 4 is an enlarged side elevation view in partial cross section of the distal portion of an endoscopic instrument similar to that of FIG. 1 including the clevis and end effectors;

FIG. 6b is a transparent side elevation view of the assembled mold and insert of FIGS. 6 and 6a.

DETAILED DESCRIPTION OF THE PREFERRED EMBODIMENTS

Figure 4A:
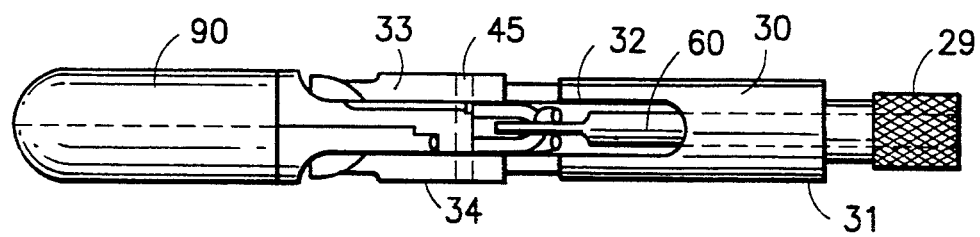
FIG. 4a is an enlarged top view of the clevis and end effectors of FIG. 4.

Referring now to FIG. 1, an endoscopic surgical instrument 10 broadly comprises an aluminum tube 15 surrounded by a peripheral insulating shrink wrap layer of plastic 20, a clevis means 30, end effectors 40, actuating means 50, and a push rod 60. The clevis means 30 is preferably a separately formed aluminum piece which fixedly engages aluminum tube 15 as described in more detail in previously incorporated U.S Pat. No. 5,192,298. The clevis 30 also engages the end effectors 40 which are pivotally engaged to clevis 30 at pivot pin 45. The end effectors 40 are preferably formed of investment cast bronze as disclosed co-owned U.S. Pat. No. 5,133,727 which is hereby incorporated herein by reference. The push rod 60, which is also preferably formed of aluminum, is engaged at its distal end 65 to the end effectors 40 and is connected at 70, at its proximal end to a manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the endoscopic instrument 10 is inserted with the blades or graspers 90, 92 of the end effector 40 in the closed position, past a gasket (not shown) of a trocar tube (not shown) and into the trocar tube. Upon the distal portion of the instrument 10 exiting the trocar tube, the blades 90, 92 can be opened and closed by reciprocal motion of push rod 60 which results from operation of the manual actuating means 50. As is discussed more fully in previously incorporated U.S Pat. No. 5,192,298, the clevis effectively translates the reciprocal motion of the push rod 60 into the end effector means action.

While the gasket of the trocar tube is provided to prevent fluids from exiting the surgical site, as discussed above, a fluid path exists inside the tube 15 of the endoscopic instrument 10. In order to prevent fluids from flowing through the tube 15, an elastomeric seal 100 is provided in the tube 15. According to a first embodiment of the invention, the elastomeric seal 100 is located proximal of the clevis 30, but preferably toward the distal end of tube 15. FIGS. 1a and 1b show this more clearly. FIG. 1a is a magnified view of the seal 100 showing its position inside tube 15 and around push rod 60. FIG. 1b is a similar view but with the push rod 60 removed in order to better see the seal 100. The seal 100 is a generally cylindrical body having an axial bore 102 and a radially inward extending protrusion or ring 104 located at the middle of the seal 100. The seal 100 is dimensioned so that it fits snugly inside tube 15 and the axial bore 102 is dimensioned to accept the push rod 60. A ring 104 snugly engages the push rod 60 so that upon axial movement of the push rod, a radially outward force is applied by the seal 100 to the tube 15. This outward force helps keep the seal 100 from axially moving within the tube 15.

FIG. 2 shows a magnified cross sectional view of the seal 100 and FIG. 2a shows a section through line A—A in FIG. 2. According to a presently preferred embodiment, for use inside tubes of a 10 mm laparoscopic instrument where the inner diameter of the tube is approximately 0.288 inches, the overall length of the seal 100 is preferably approximately 0.4 inches and the overall diameter of the seal is preferably approximately 0.292 inches. The axial bore 102 has a diameter of approximately 0.198 inches except for the portion which is reduced by the protruding ring 104. With the outer diameter of the push rod 60 being approximately 0.094 inches, ring 104 extends radially inward from a central position in the axial bore 102 to reduce the inner diameter to approximately 0.085 inches over an axial length of approximately 0.035 inches. Ring 104, as shown, has a rounded inner surface 104a and may assume the shape of a torus embedded in the axial bore of the seal. It will be understood from the forgoing dimensions that the Figures herein are not drawn to scale.

FIG. 3 shows a mold 150 for use in making the seal 100 described above and FIG. 3a shows an insert 200 for use with mold 150. The elastomeric fluid seal 100 of the invention is preferably made from a 1:10 ratio mixture of curing agent and Dow Corning SILASTIC MDX4-4210 medical grade elastomer which when cured provides a translucent silicone rubber which has enough elasticity to elongate approximately 100% without tearing. In accord with the invention, SILASTIC is mixed according to Dow Corning's specifications and placed in a mold 150. The mold 150 is a substantially cylindrical body having and inner cylindrical chamber 152 which is dimensioned according to the outer dimensions of the fluid seal 100 as described above, e.g. 0.4 inches deep with a diameter of 0.292 inches.

After the SILASTIC is placed in the mold 150, a mold insert 200 is introduced. The mold insert 200 comprises a center rod 202 with a bevel 204 and a centering cap 206. It will be appreciated that the diameter of the center rod 202 corresponds to the inner diameter of the axial bore 102 of fluid seal 100 and that the dimensions of bevel 204 correspond to the dimensions of ring 104.

After the insert is placed in the mold containing the mixed SILASTIC, the mold is capped and placed in an oven at 100° C. for approximately 15±1 minutes in accordance with Dow Corning's specifications. The mold is then removed and allowed to cool at room temperature for approximately 10 minutes. The mold is then opened and the molded fluid seal is carefully removed at which point the seal has an elasticity allowing about 100% elongation without tearing. The seal is then allowed to air set for approximately four hours before being placed in the endoscopic instrument.

In assembling the endoscopic instrument, the seal 100 is typically lightly forced into the distal end of tube 20 prior to the clevis 30 being inserted in the tube, and prior to the push rod 60 being inserted through the seal and into the tube. For ease of insertion, the seal 100 is located near the distal end of the tube 20, although it could be otherwise located. As mentioned above, because the protruding ring 104 of the seal is located in the middle of the seal, the seal remains in its position even upon reciprocal movement of the push rod 60 which extends therethrough.

Figure 4B:
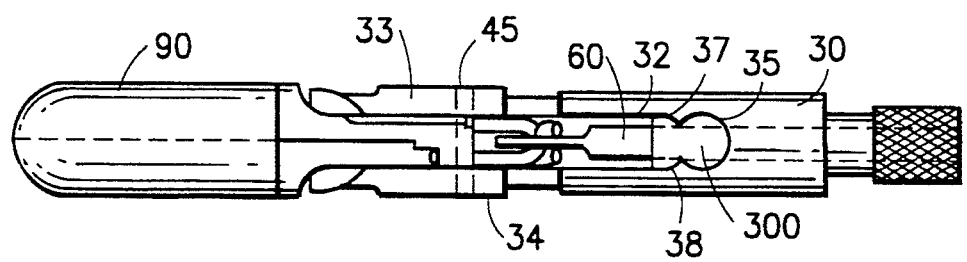
FIG. 4b is, a view similar to FIG. 4a but showing a second embodiment of the fluid seal of the invention.

FIGS. 4 and 4a show an enlarged detail of the distal end of an endoscopic instrument similar to the one shown in FIG. 1, but having a 5 mm tube, and FIGS. 4b through 5a show details of a second embodiment of the fluid seal of the invention for particular use with endoscopic instruments having 5 mm tubes. Referring now to FIGS. 4 and 4a, the distal end of the endoscopic instrument has a clevis 30 which carries a pair of end effectors 40 mounted on a pivot pin 45. The clevis 30 generally comprises a cylindrical tube 31 having a diameter of approximately 5 mm with a U-shaped cut-out 32 defining a pair of arms 33, 34 between which the end effectors 40 are mounted and coupled to the push rod 60. A roughened or serrated reduced diameter proximal portion 29 is provided on the clevis for coupling via force fitting and/or crimping with a 5 mm tube 20. A second embodiment of the fluid seal 300 is mounted in the clevis 30 by modifying the clevis as shown in FIG. 4b.

As seen in FIG. 4b, a through bore 35 is drilled in the tube 31 of clevis 30 adjacent the proximal end of the U-shaped cut-out 32. The bore 35 is preferably approximately 0.1 inches in diameter and passes completely through the clevis tube 31 (i.e., the bore cuts holes in both opposite walls of the clevis tube). As seen in FIG. 4b, the center of bore 35 is arranged close enough to cut-out 32 so that the bore overlaps a portion of the cut-out by approximately 0.03 inches leaving a pair of intersecting walls 37, 38 partially separating cut-out 32 from bore 35. A SILASTIC fluid seal 300 as described in detail hereainfter is inserted in the bore 35 and extends partially into the cut-out 32.

Figure 5:
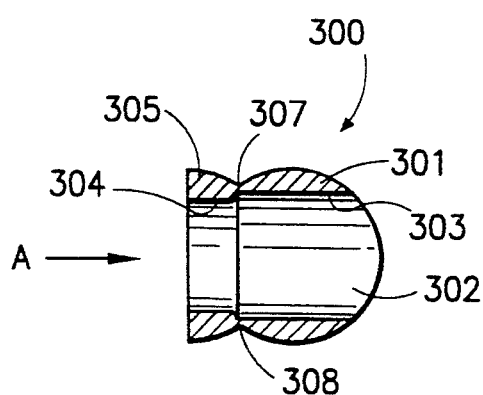
FIG. 5 is an enlarged longitudinal cross sectional view of the fluid seal of FIG. 4b.
Figure 5A:
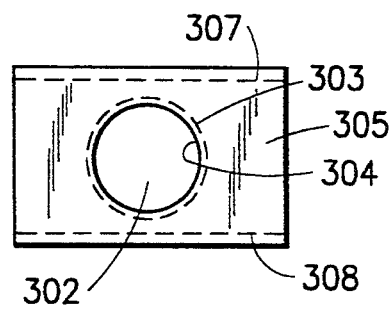
FIG. 5a is an end view of the fluid seal of FIG. 5 looking in the direction A in FIG. 5.

FIGS. 5 and 5a show SILASTIC fluid seal 300 in greater detail. Seal 300 comprises a first cylindrical portion 301 and a second semi-cylindrical portion 305. Both portions have a radius of approximately 0.051 inches and a height of approximately 0.148 inches. Their respective centers are offset by approximately 0.07 inches and they are molded as a unitary piece having overall dimensions of approximately 0.148 inches tall, 0.102 inches wide, and 0.120 inches long. As seen in FIGS. 5 and 5a, the first and second portions of the seal 300 are delimited by lines of intersection 307, 308. A longitudinal hole 302 extends through the length of the seal for receiving the push rod 60 as shown in FIG. 4b. A first portion 303 of hole 302 which passes through the first cylindrical portion 301 has a relatively large diameter of approximately 0.07 inches. A second portion 304 of hole 302 which passes through second semi-cylindrical portion 305 has a reduced diameter of approximately 0.062 inches.

Comparing FIGS. 4b and 5, it will be appreciated that the seal 300 is designed to fit snugly into the bore 35 and a portion of the cut-out 32 of the clevis 30. The first cylindrical portion 301 of the seal fits into the bore 35 of the clevis while the second semi-cylindrical portion 305 fits into a portion of the cut-out 32 of the clevis. The intersecting walls 37, 38 of the clevis embrace the lines of intersection 307, 308 in the seal 300.

Figure 6:
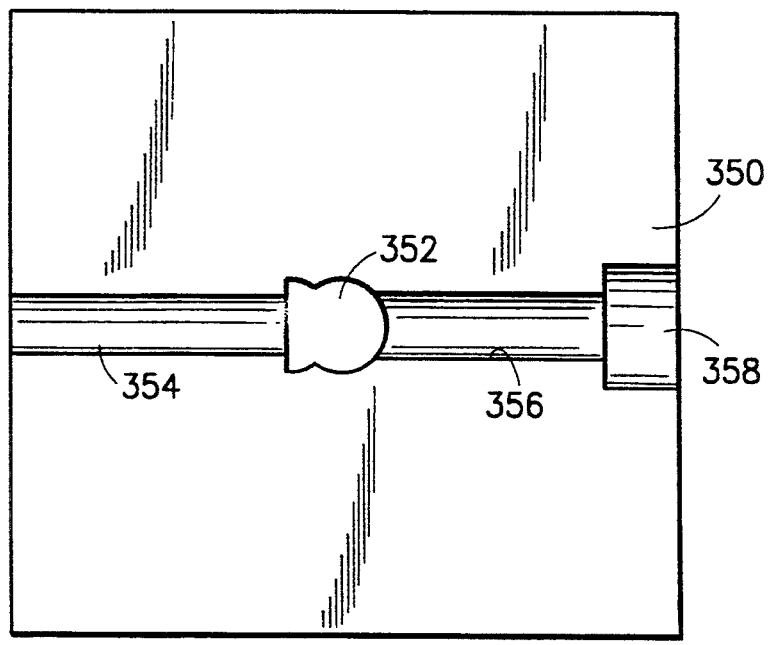
FIG. 6 is a top plan view of a bottom half of a mold for making the second embodiment of the fluid seal of the invention.
Figure 6A:
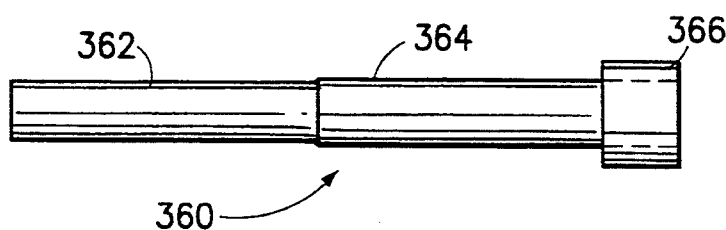
FIG. 6a is a side elevation view of a mold insert used with the mold of FIG. 6.
Figure 6B:
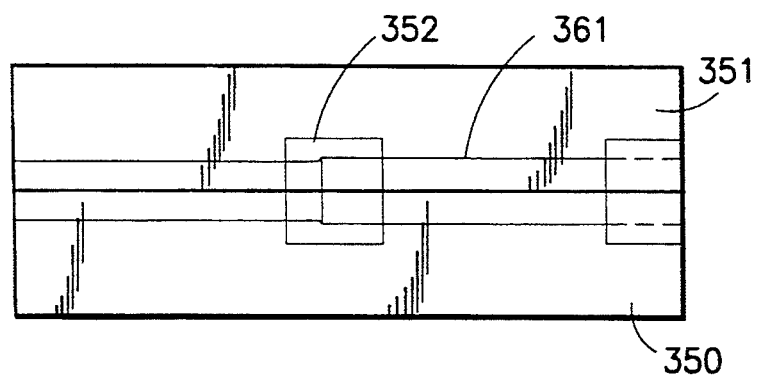

FIGS. 6, 6a, and 6b show a mold and mold insert for making the fluid seal 300 described above. The mold comprises a bottom plate 350 and a top plate 351 which when assembled define the seal forming space 352 and a three stepped through bore 361. The mold insert 360 comprises a three stepped cylinder having a narrow diameter portion 362, a slightly larger diameter portion 364 and a relatively wide removable collar portion 366. SILASTIC is mixed in the same manner as described above and poured into the assembled mold. Then, the insert is placed inside the mold so that the narrow diameter portion 362 fits inside narrow part 354 of bore 361 and larger diameter portion 364 fits inside wider part 356 of bore 361. Preferably, an additional amount of SILASTIC is then poured into the wide opening 358 of bore 361 and the mold is closed prior to heating and cooling as described above.

Those skilled in the art will appreciate that rather than using the molds and mold inserts and described with reference to FIGS. 3, 3a, and 6, 6a, and 6b, injection molding or other molding techniques could be utilized to make the seals.

In assembling an endoscopic instrument using the second embodiment of the seal 300, the seal 300 is slid laterally into the clevis 30, with the cylindrical portion 301 of seal slid into bore 35, and the semi-cylindrical portion 305 slid into the proximal end of cut-out 32. Because walls 37, 38 of the clevis are of reduced inner diameter relative the bore 35 and the cut-out, the walls 37, 38 hold the seal 300 in place at the line of intersection 307, 308 location of reduced outer diameter. After the seal 300 is in place, the push rod 60 may be inserted therethrough, with at least inner surface 304 of the seal making sealing contact therewith. The remainder of the endoscopic instrument may then be assembled. In use, movement of the push rod 60 through the seal 300 cannot force the seal 300 out of its location due to the reduced diameter walls 37, 38 of the clevis 30 and the reduced diameter lines of intersection 307, 308 of the seal 300.

There have been described and illustrated herein elastomeric fluid seals for use in endoscopic instruments, and endoscopic instruments incorporating such seals and methods of making the seals. While particular preferred embodiments of the invention and methods have been described, it is not intended that the invention be limited thereto, as it is intended that the invention be as broad in scope as the art will allow and that the specification be read likewise. Thus, while particular dimensions have been disclosed with reference to the seal as used in a particular endoscopic instrument, it will be appreciated that other dimensions might be utilized when using the seal in other endoscopic instruments. Also, while particular endoscopic instruments incorporating the fluid seals have been shown by way of example, it will be recognized that other types of endoscopic instruments could be used with similar results obtained. Moreover, while particular configurations have been disclosed in reference to the radially inward extending ring, it will be appreciated that other configurations could be used as well. Furthermore, while the fluid seal has been disclosed as consisting of a particular type of elastomer, it will be understood that different materials can achieve the same or similar function as disclosed herein. It will therefore be appreciated by those skilled in the art that yet other modifications could be made to the provided invention without deviating from its spirit and scope as so claimed.

We claim:

1. In an endoscopic instrument having an outer tube, a push rod extending at least partially through said outer tube with an annular space being defined between said push rod and said outer tube, end effector means coupled to said push rod and coupled to said outer tube by a clevis having a substantially U-shaped cut-out, and actuation means coupled to said push rod for effecting reciprocal motion to said push rod and thereby causing said end effector means to move, an improvement, comprising:

an elastic sealing means for sealing said annular space between said tube and said push rod and preventing fluid flow through said annular space, said elastic sealing means having an outer surface contacting an inner surface portion of said clevis and an inner surface portion contacting an outer surface portion of said push rod, wherein:

said clevis includes a radial bore overlapping a proximal portion of said cut-out and said elastic seal straddles said bore and said proximal portion of said cut-out.

2. In an endoscopic instrument according to claim 1, wherein:

said elastic seal comprises a unitary member having a substantially cylindrical portion and a connected, adjacent substantially semi-cylindrical portion, said substantially cylindrical portion residing in said radial bore of the clevis, and said substantially semi-cylindrical portion residing in the proximal end of said cut-out.

3. In an endoscopic instrument according to claim 2, wherein:

said elastic seal has a stepped throughbore through which said push rod moves.

4. In an endoscopic instrument according to claim 3, wherein:

said stepped throughbore has a narrower diameter portion inside said substantially semi-cylindrical portion of said elastic seal.

5. An endoscopic instrument comprising:
a) a hollow tube having an inner surface;
b) at least one end effector element pivotally coupled to said hollow tube;
c) a rod extending at least partially through said hollow tube and coupled to said at least one end effector element;
d) actuating means for engaging said rod and for imparting reciprocal motion to said rod relative to said tube which reciprocal motion causes pivotal motion of said at least one end effector;
e) a clevis coupled to said a first end of said hollow tube and to said at least one end effector means, said clevis comprising a tube with a U-shaped cut-out; and
f) an elastomeric fluid seal located in said clevis, said elastomeric fluid seal having an outer surface contacting a portion of an inner surface of said clevis, and an inner surface portion contacting and surrounding a portion of an outer. Surface of said rod, wherein, said clevis includes a radial bore overlapping a proximal portion of said cut-out and said elastic seal straddles said bore and said proximal portion of said cut-out.

6. In an endoscopic instrument according to claim 5, wherein:

said elastic seal comprises a unitary member having a substantially cylindrical portion and an overlapping substantially semi-cylindrical portion, said substantially cylindrical portion residing in said radial bore and said substantially semi-cylindrical portion residing in said bottom of said cut-out.

7. In an endoscopic instrument according to claim 6, wherein:

said elastic seal has a stepped throughbore through which said push rod is movable.

8. In an endoscopic instrument according to claim 7, wherein:

said stepped throughbore has a narrower diameter portion inside said substantially semi-cylindrical portion of said elastic seal.

* * * * *